United States Patent [19]
Landrau et al.

[11] Patent Number: 5,512,293
[45] Date of Patent: Apr. 30, 1996

[54] ORAL SUSTAINED RELEASE DRUG DELIVERY DEVICE

[75] Inventors: Felix A. Landrau, San Jose; Patricia S. Campbell, Palo Alto; Arthur W. Hall, Alviso; Juan M. E. Harrison, Mountain View, all of Calif.

[73] Assignee: ALZA Corporation, Palo Alto, Calif.

[21] Appl. No.: 164,181

[22] Filed: Dec. 9, 1993

Related U.S. Application Data

[63] Continuation of Ser. No. 919,003, Jul. 23, 1992, abandoned.
[51] Int. Cl.$^6$ ............... A61L 15/24; A61K 9/70; A61K 47/32
[52] U.S. Cl. ............ 424/449; 424/486; 424/435; 424/448
[58] Field of Search ............... 424/486, 449, 424/435, 425

[56] References Cited

U.S. PATENT DOCUMENTS

| | | | |
|---|---|---|---|
| 3,921,636 | 11/1975 | Zaffaroni | 128/260 |
| 3,972,995 | 8/1976 | Tsuke et al. | 424/447 |
| 4,069,307 | 1/1978 | Higuchi et al. | 424/22 |
| 4,177,256 | 12/1979 | Michaels et al. | 424/22 |
| 4,186,184 | 1/1980 | Zaffaroni | 424/14 |
| 4,209,505 | 6/1980 | Mikhail | 424/54 |
| 4,564,364 | 1/1986 | Zaffaroni et al. | 604/897 |
| 4,938,963 | 7/1990 | Parnell | 424/440 |
| 4,983,378 | 1/1991 | Parnell | 424/440 |
| 5,021,053 | 6/1991 | Barclay et al. | 604/892.1 |
| 5,053,032 | 10/1991 | Barclay et al. | 604/892.1 |
| 5,095,054 | 3/1992 | Lay et al. | 424/451 |

OTHER PUBLICATIONS

Epstein et al, Synergistic effect of sialagogues in management of xerostomia after radiation therapy, Oral Surg., vol. 64, No. 2, pp. 179–182, Aug. 1987.
Rhodus, et al, Effects of pilocarpine on salivary flow in patients with sjogren's syndrome, Oral Surg Oral Med Oral Pathol, vol. 72, No. 5, pp. 545–549, Nov. 1991.
P. C. Fox, Systemic Therapy of Salivary Gland Hypofunction, J Dent Res, vol. 66, Special Issue, pp. 689–692, Feb. 1987.
Fox et al., Pilocarpine for the treatment of xerostomia associated with salivary gland dysfunction, Oral Surg, vol. 61, No. 3, pp. 243–248, Mar. 1986.
Wolff, et al, Pretherapy Interventions to Modify Salivary Dysfunction, NCI Monographs, No. 9, pp. 87–90, 1990.
Fox, et al, Pilicarpine Treatment of Salivary Gland Hypofunction and Dry Mouth (Xerostomia), Arch Intern Med. vol. 151, pp. 1149–1152, Jun. 1991.
Mandel, et al, The Effect of Pharmacologic agents on salivary secretion and composition in man, I. Pilocarpine, Atropine & Anticholinesterases, Journ of Oral Therapeutics, vol. 4, No. 3, pp. 192–199, Nov. 1967.
Greenspan, et al, Effectiveness of Pilocarpine in Postradiation Xerostomia, Cancer, vol. 59, pp. 1123–1125, Mar. 15, 1987.
Saunte, Quantification of salivation, nasal secretion and tearing, Cephalalgia 3, pp. 159–173, 1983.
Epstein, et al, Management of xerostomia, Scientific Journal, vol. 58, No. 2, pp. 140–143, Feb. 1992.
Weaver, et al, Salivary Flow Induction by Buccally–Applied Pilocarpine in Anesthesized Dogs, Journal of Dental Research, vol. 70, Special Issue, Abstracts, p. 314.
Baker, Controlled Release of Bioactive materials, pp. 177–187, Academica Press, 1980.
Chien, et al, Release from Polymeric Delivery Devices II, J. Pharm Sci, vol. 63, No. 4, pp. 515–519, Apr. 1974.

Primary Examiner—Edward J. Webman
Attorney, Agent, or Firm—Richard T. Ito; Steven F. Stone; Edward L. Mandell

[57] ABSTRACT

This invention pertains to a sustained release delivery device for delivering a beneficial agent into the oral cavity of a patient. More particularly, the invention relates to a device comprising about 0.1% to about 20% by weight beneficial agent, about 40% to about 95% by weight ethylene vinyl acetate copolymer having a vinyl acetate content of about 4% to about 80% and about 1% to about 60% by weight polyvinyl pyrrolidone.

25 Claims, 4 Drawing Sheets

ORAL SUSTAINED RELEASE DRUG DELIVERY DEVICE

This application is a continuation of application Ser. No. 07/919,003, filed Jul. 23, 1992, now abandoned and benefit of the filing date of said earlier filed application is claimed under 35 U.S.C. § 120.

TECHNICAL FIELD

This invention pertains to a sustained release delivery device for delivering a beneficial agent into the oral cavity of a patient. More particularly, the invention relates to a device comprising about 0.1% to about 20% by weight beneficial agent, about 40% to about 95% by weight ethylene vinyl acetate copolymer having a vinyl acetate content of about 4% to about 80% and about 1% to about 60% by weight polyvinyl pyrrolidone.

BACKGROUND ART

When administering a drug buccally (i.e., by absorption of the drug through the buccal tissues of the mouth) a number of conditions are present which makes it difficult to effectively deliver drug in a therapeutically effective amount for a prolonged period of time (e.g., for periods greater than several minutes). For example, when a patient is given a drug-containing lozenge, there is a natural tendency to suck and chew on the lozenge thereby effectively reducing the time period during which the drug can be buccally administered by the lozenge. This has been a particular problem in treating diseases of the mouth which require constant local administration of the drug. In addition, the action of saliva and swallowing by the patient effectively reduces the concentration of drug along the buccal membranes of the oral cavity and further causes much of the drug to be swallowed, in many cases rendering it inactive upon encountering the low pH environment of the stomach. One such disease that requires constant administration of drug is xerostomia.

Xerostomia is a condition in which salivary glands do not produce sufficient quantities of saliva. Cases of xerostomia may vary from the mild, in which only slight dryness is experienced, to severe cases in which the patient will have serious problems with swallowing, speech, digestion, and the like. There are a number of causes of xerostomia, including physiological, psychological, pharmacological (e.g., as a common side effect of many medications), or as a result of radiotherapy.

Until recently, the treatments for xerostomia have had significant drawbacks. For example, symptoms of mild xerostomia can be somewhat alleviated by consumption of fluids, hard candy, and throat lozenges. However, fluids or candy are typically not effective with more severe cases of xerostomia, and more importantly, they do not provide long lasting relief.

Another recommended method of treating xerostomia buccally is by placing 2–4 drops of pilocarpine ophthalmic drops on the tongue four times daily, Epstein et al., "Management of Xerostomia," *Scientific Journal*, Vol. 58, No. 2, February 1992. Unfortunately, when pilocarpine is administered, either by drops or by a mouthrinse, the drug is cleared from the mouth in a matter of minutes, U.S. Pat. No. 4,209,505.

U.S. Pat. No. 4,983,378 describes the delivery of Yerba Santa extract by gum or lozenge form. While the duration of drug delivery is increased somewhat using slowly dissolving lozenges, typically these release drug for no more than about 15 to 20 minutes. Accordingly, these dosage forms require frequent repetitive dosing in order to effectively treat the condition.

In response to the problem of short duration of drug delivery from rinses and lozenges, it is necessary to extend delivery over a long period of time in a predictable fashion. Previous devices utilize, in one form or another, release rate controlling barriers or membranes interposed between the source of the drug and the environment of use to control release rates. While such devices can be designed to produce extremely precise release rates, their structure is relatively complex, which complexity adds to the cost of the device.

In particular, the use of an osmotic pump to deliver mediation to the buccal tissues has been taught. See U.S. Pat. Nos. 5,053,032 and 5,021,053. Unfortunately, the membrane surrounding the osmotic pump can burst when aggressively chewed, thus releasing the entire dose present in the device. This presents a safety problem, when the release of the entire dose of a drug can cause severe adverse side effects. Additionally, an osmotic pump device requires a sufficient amount of water to operate and drive the pump. In patients, who do not produce sufficient quantities of saliva, the osmotic pump device will not operate.

Other devices have been taught where precise control is not required. It has been known to disperse the biologically active agent in a polymeric matrix which is then placed in the environment of use and the active agent released therefrom by diffusion. The rate of release of a dispersed active agent at a concentration equal to or less than saturation from such systems normally will vary inversely with the square root of time ($t^{-1/2}$) that the system is in operation. U.S. Pat. No. 4,069,307. Such systems, accordingly, are characterized by an initial high release rate which then decreases relatively rapidly and continuously over the lifetime of the device. This is due to the depletion of the drug from the matrix which reduces the concentration gradient between the matrix and the surrounding environment. Such devices do not provide a sustained controlled rate of delivery for a prolonged period of time.

Since simply dispersing an active agent through a matrix has significant safety and cost advantages, various approaches have been proposed to improve the release characteristics without resorting to the use of rate controlling membranes. Geometrical approaches have been suggested, *Controlled Release of Bioactive Materials*, Edited by Richard Baker, p. 177–187, Academic Press, New York (1980), as have systems based on the relationship between solubility and diffusion coefficient, Chien et al., *Controlled Drug Release From Polymeric Delivery Devices II: Differentiation Between Partition Controlled and Matrix Controlled Drug Release Mechanisms*, J. Pharm. Sci., Vol. 63, No. 4, p. 515–519 (April 1974). It has also been proposed to vary the concentration between the core and the outer layer or to have a depleted zone containing the agent at a concentration no greater than saturation and a non-depleted zone containing the agent dispersed in the matrix at a uniform concentration greater than saturation, U.S. Pat. No. 4,564,364. Other proposed devices have a plurality of reservoirs containing drug distributed through a matrix, U.S. Pat. No. 3,921,636.

While these approaches can improve the release characteristics of the device, the manufacturing techniques required to obtain the desired concentration gradient, either by forming separate compositions having different concentrations of solute dispersed in the matrix and thereafter sequentially forming the end item, by sequentially depositing additional amounts of the active agent onto a substrate, by extracting the surface of the finished device, or by forming microcapsules around the drug reservoir; may closely approach the cost associated with manufacturing a rate controlling membrane system having superior properties.

Thus, there has been a clear need in the art of treating oral disease, such as xerostomia, for a dosage form which is able to continuously deliver therapeutically effective amounts of drug or other beneficial agent into the oral cavity for extended periods of time, i.e. periods greater than about 15 to 20 minutes, with a minimal amount of water and low cost of manufacturing.

DISCLOSURE OF THE INVENTION

Accordingly, it is an object of this invention to provide a monolithic homogenous sustained release delivery device, for the controlled delivery of a beneficial agent to the oral cavity of an animal, having improved release characteristics.

It is another object of this invention to provide a sustained release delivery device, for the controlled delivery of a beneficial agent to the oral cavity of an animal, in particular a human, for an extended period of time by providing a device that will not release the entire dosage of the beneficial agent when aggressively chewed.

It is another object of the invention to provide a sustained release delivery device for the controlled delivery of a beneficial agent to the oral cavity of an animal, in particular a human, for an extended period of time, by providing a device that requires a minimal amount of water to operate.

It is an object of this invention to provide a method of treating oral disease by the controlled delivery of a beneficial agent at a pharmaceutically effective rate to the oral cavity of an animal, and in particular a human, for an extended period of time using a monolithic homogenous sustained release delivery device having improved release characteristics.

It is yet another object of the invention to provide a method of treating oral disease by the controlled delivery of a beneficial agent at a pharmaceutically effective rate to the oral cavity of an animal, and in particular a human, for an extended period of time using a sustained release delivery device that will not release the entire dose of beneficial agent when aggressively chewed.

It is a further object of the invention to provide a method of treating oral disease by the controlled delivery of a beneficial agent at a pharmaceutically effective rate to the oral cavity of an animal, and in particular a human, for an extended period of time using a sustained release delivery device that requires a minimal amount of water to operate.

Other objects, features and advantages of the invention will be more apparent to those versed in the art from the following detailed specification taken in conjunction with the figures and the accompanying claims.

As used herein, the term "pilocarpine" is used to designate pilocarpine, acid addition salts of pilocarpine, such as pilocarpine nitrate, and the related compounds thereof. Preferably, the device of this invention contains pilocarpine as the free base.

As used herein, the term "matrix" refers to a well-mixed composite of ingredients fixed into a shape.

This invention concerns a sustained release delivery device for controlled delivery of a beneficial agent into the oral cavity of an animal, such as a human. The device comprises about 0.1% to about 20% by weight beneficial agent, about 40% to about 95% by weight ethylene vinyl acetate copolymer having a vinyl acetate content of about 4% to about 80% and about 1% to about 60% by weight polyvinyl pyrrolidone. Preferably, the device comprises about 0.1% to about 20% by weight beneficial agent, about 45% to about 80% by weight ethylene vinyl acetate copolymer having a vinyl acetate content of about 20% to about 50%, and about 10% to about 50% by weight polyvinyl pyrrolidone. More preferably, the device comprises about 1% to about 20% by weight pilocarpine, about 65% to about 80% by weight ethylene vinyl acetate copolymer having a vinyl acetate content of about 25% to about 55%, and about 15% to about 25% by weight polyvinyl pyrrolidone. Each device has a size and shape allowing it to be comfortably retained in the oral cavity for an extended period of time.

BRIEF DESCRIPTION OF THE DRAWINGS

In the drawings (which are not drawn to scale) and the specification, like parts in related figures are identified by like numerals.

DETAILED DESCRIPTION OF THE INVENTION AND PREFERRED EMBODIMENTS

According to our invention, we are able to modify the release rate from a monolithic system from the typical $t^{-1/2}$ relationship to produce systems which release at a rate more constant with time. This result is accomplished according to our invention with a device comprising ethylene vinyl acetate copolymer and polyvinyl pyrrolidone.

When drug is blended into an ordinary monolithic system at, or below, saturation levels, the drug will diffuse out of the system at a continuously decreasing rate that is a function of the square root of time ($t^{-1/2}$ diffusion kinetics). In our invention, when the drug is blended into the monolithic system of ethylene vinyl acetate copolymer and polyvinyl pyrrolidone and is placed in an aqueous environment, the drug will initially mimic the $t^{-1/2}$ diffusion kinetics of an ordinary monolithic system. However, at some time, the system absorbs enough water to progressively increase its permeability and thus provides a flat sustained release rate profile.

Figure 1:
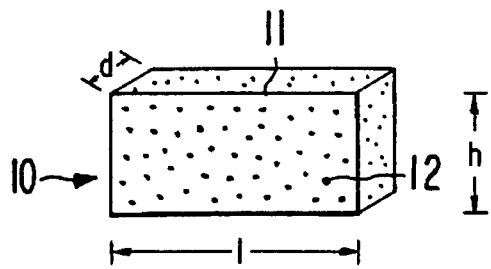
FIG. 1 is a side cross-sectional view of a drug delivery device of this invention.

Turning now to the drawings, one example of a sustained release delivery device is shown in FIG. 1 and is indicated by the numeral 10. Device 10 can be comprised of a solid matrix 11 comprising about 40% to about 95% by weight ethylene vinyl acetate copolymer having a vinyl acetate content of about 4% to about 80% and about 1% to about 60% by weight polyvinyl pyrrolidone, which also serves as a beneficial agent reservoir, having about 0.1% to about 20% by weight beneficial agent 12 distributed therethrough.

Figure 2:
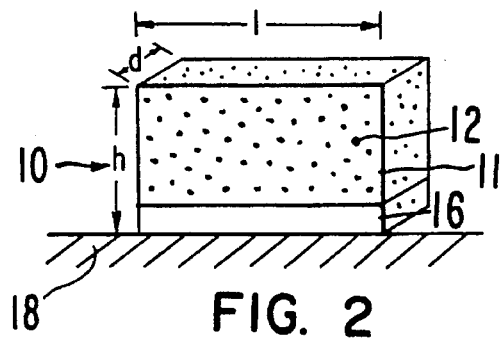
FIG. 2 is a side cross-sectional view of another embodiment of the invention.

FIG. 2 illustrates another important use of the invention. Device 10 has an adhesive layer 16 that allows the system to be anchored to the mouth, minimizing the risk of swallowing or aspirating the device. This type of system can be worn by sleeping patients or those who have motor coordination difficulties. Device 10 of the invention comprises a solid matrix 11 comprising about 40% to about 95% by weight ethylene vinyl acetate copolymer having a vinyl acetate content of about 4% to about 80% and about 1% to about 60% by weight polyvinyl pyrrolidone, which also serves as a beneficial agent reservoir, having about 0.1% to about 20% by weight beneficial agent 12 distributed therethrough. Device 10 adheres to the surface of the mucosa 18 by means of the adhesive layer 16. A strippable release liner (not shown in FIG. 2) is normally provided along the exposed surface of adhesive layer 16 and is removed prior to application of device 10 to the mucosa 18.

Figure 3:
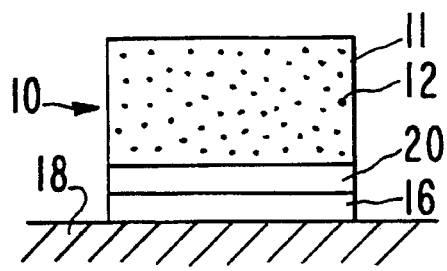
FIG. 3 is a side cross-sectional view of still another embodiment of the invention.

As illustrated in FIG. 3, this embodiment of the invention further includes a barrier 20 that is impermeable to beneficial agent 12. Device 10 comprises a solid matrix 11 comprising about 40% to about 95% by weight ethylene vinyl acetate copolymer having a vinyl acetate content of about 4% to about 80% and about 1% to about 60% by weight polyvinyl pyrrolidone, which also serves as a beneficial agent reservoir, having about 0.1% to about 20% by weight beneficial agent 12 distributed therethrough. Device 10 adheres to the surface of the mucosa 18 by means of the adhesive layer 16. A barrier 20 is sandwiched between adhesive 16 and matrix 11. Barrier 20 prevents beneficial agent 12 from being delivered directly to the mucosa. This is important with potentially irritating beneficial agents, since the beneficial agent is first diluted by the saliva before contacting the mucosa in this embodiment. Preferably, barrier 20 is made of cellophane, cellulose acetate, ethyl cellulose, plasticized vinyl acetate-vinyl chloride copolymers, polyethylene terephthalate, nylon, high and low density polyethylene, polypropylene, metallized polyester films, polyvinyllidene chloride, coated flexible fibrous backing or aluminum foil.

Figure 4:
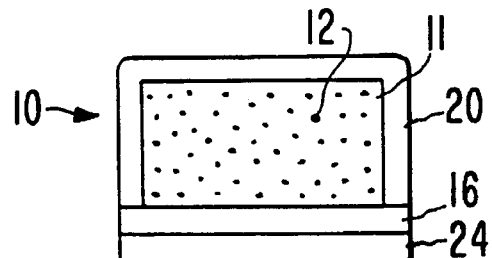
FIG. 4 is a side cross-sectional view of yet another embodiment of the invention.

As shown in FIG. 4, barrier 20 may overlay device 10. Device 10 comprises a solid matrix 11 comprising about 40% to about 95% by weight ethylene vinyl acetate copolymer having a vinyl acetate content of about 4% to about 80% and about 1% to about 60% by weight polyvinyl pyrrolidone, which also serves as a beneficial agent reservoir, having about 0.1% to about 20% by weight beneficial agent 12 distributed therethrough. Barrier 20, which is impermeable to beneficial agent 12, is provided adjacent one surface of matrix 11. Adhesive layer 16 is provided adjacent the other surface of matrix 11 and maintains the device on the mucosa. In this embodiment, adhesive layer 16 must be water permeable. Additionally, beneficial agent transport through layer 16 must be faster than beneficial agent transport from matrix 11, in order to allow beneficial agent delivery rates to be controlled by the reservoir matrix 11. A strippable release liner 24 is also provided with device 10 and is removed just prior to application of device 10 to the skin.

Figure 5:
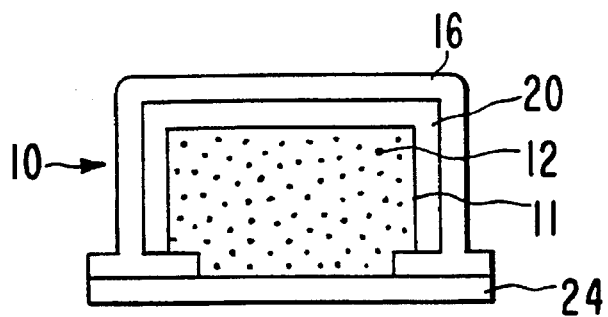
FIG. 5 is a side cross-sectional view of another embodiment of the invention.

Alternatively, as shown in FIG. 5, adhesive layer 16 overlays matrix 11. Device 10 includes a solid matrix 11 comprising about 40% to about 95% by weight ethylene vinyl acetate copolymer having a vinyl acetate content of about 4% to about 80% and about 1% to about 60% by weight polyvinyl pyrrolidone, which also serves as a beneficial agent reservoir, having about 0.1% to about 20% by weight beneficial agent 12 distributed therethrough. Barrier 20, which is impermeable to beneficial agent 12, is provided adjacent one surface of matrix 11. Adhesive layer 16 overlays barrier 20 and maintains the device on the mucosa. Adhesive layer 16 may be fabricated together with, or provided separately from, the remaining elements of the device. With certain formulations, the adhesive layer 16 may be preferable to the in-line contact adhesive 16, shown in FIG. 4. Barrier 20 is preferably slightly larger than matrix 11, and in this manner prevents the materials in matrix 11 from adversely interacting with the adhesive in overlay. The outer edges of adhesive layer 16 overlay the edges of matrix 11 and are joined along the perimeter with the outer edges of barrier 20 in a fluid-tight arrangement. This sealed reservoir may be effected by heat, pressure, fusion, adhesion, an adhesive applied to the edges, or other methods known in the art. A strippable release liner 24 is also provided with device 10 and is removed just prior to application of device 10 to the skin.

The embodiments of FIGS. 3, 4 and 5 are particularly suited to: 1) beneficial agents that are to be delivered to a local site, 2) beneficial agents that are sensitive or unstable in the oral cavity environment, 3) systemic beneficial agents that need high local concentrations on the mucosa to be absorbed efficiently, or 4) to beneficial agents that have bad tastes. Additionally, in the embodiments of FIGS. 3, 4 and 5, barrier 20 may be permeable to water vapor. This design maximizes transport of water to matrix 11 and increases the rate of beneficial agent release. This embodiment is particularly suited for agents that have large molecular weights, low water solubility or high melting points.

The term "beneficial agent", as used herein, includes any agent or compound, that can be delivered from the device into the oral cavity to produce a beneficial and useful result, including any physiologically (i.e., denotes the administration of a beneficial agent to produce normal levels or functions) or pharmacologically active substance (i.e, denotes variations in response to amount of beneficial agent administered to host) that produces a local or systemic effect when administered to the oral cavity of an animal. The agent can be insoluble or very soluble in the exterior fluid. The beneficial agents that can be delivered includes inorganic and organic drugs without limitations, those drugs that act on the central nervous system, depressants, hypnotics, sedatives, psychic energizers, tranquilizers, anticonvulsants, muscle relaxants, antiparkinson agents, analgesics, anti-inflammatory agents, local anesthetics, muscle contractants, antimicrobials, antivirals, antifungals, antimalarials, hormonal agents, contraceptives, sympathomimetics, diuretics, antiparasitics, neoplastics, hypoglycemics, ophthalmics, electrolytes, diagnostic agents, cardiovascular drugs, prostaglandins and ergoloids.

Exemplary drugs that can be delivered by the devices of this invention, include pilocarpine, nystatin, cetylpyridinium chloride, sumatriptan, nicotine, ergotamine, dihydroergotamine, chlorhexidine, clonidine, sodium fluoride, prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, atropine sulfate, methscopolamine bromide, isopropamide iodide, tridihexethyl chloride, phenformin hydrochloride, methylphenidate hydrochloride, oxprenolol hydrochloride, metoprolol tartrate, cimetidine hydrochloride, retin A, diphenidol, meclizine hydrochloride, prochlorperazine maleate, phenoxybenzamine, thiethylperazine maleate, anisindione, diphenadione erythrityl tetranitrate, digoxin, isoflurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic progestational hormones, corticosteroids, hydrocortisone, hydrocorticosterone acetate, cortisone acetate, triamcinolone, testosterone, testosterone esters, methyltesterone, 17β-estradiol, ethinyl estradiol, ethinyl estradiol 3-methyl ether, prednisolone, 17β-hydroxyprogesterone acetate, 19-nor-progesterone, norgestrel, norethindrone, progesterone, norgesterone, norethynodrel, and the like.

Examples of other drugs that can be delivered by the device include aspirin, indomethacin, naproxen, fenoprofen, sulindac, diclofenac, ibuprofen, indoprofen, nitroglycerin, propranolol, metoprolol, valproate, oxprenolol, timolol, atenolol, alprenolol, cimetidine, clonidine, imipramine, levodopa, chlorpromazine, reserpine, methyl-dopa, dihydroxyphenylalanine, pivaloyloxyethyl ester of α-methyl-dopa hydrochloride, theophylline, calcium gluconate, ferrous lactate, vincamine, diazepam, phenoxybenzamine, α-blocking agents, polypeptides, proteins, insulin and the like. The beneficial drugs are known in the art in the current Physicians' Desk Reference 1992, 46th Ed., published by Medical Economics Data, Montvale, N.J. and the like.

The beneficial agent can be in various forms, such as uncharged molecules, molecular complexes, pharmacologically acceptable salts such as hydrochloride, hydrobromides, sulfate, laurylate, palmitate, phosphate, nitrite, borate, acetate, maleate, tartrate, oleate, and salicylate. For acid drugs, salts of metals, amines or organic cations, for example, quaternary ammonium can be used. Derivatives of beneficial agents such as esters, ethers and amides can be used.

The device of the invention is manufactured by standard techniques. For example, the device can be made by solvent casting, milling and pressing or blending and extruding.

The amount of beneficial agent present in the therapeutic device and required to achieve an effective therapeutic result depends on many factors, such as the minimum necessary dosage of beneficial agent for the particular indication being treated; the solubility and permeability of the matrix, of the adhesive layer, if present; and the period of time for which the device will be fixed to the mucosa or held in the oral cavity. The minimum amount of beneficial agent is determined by the requirement that sufficient quantities of beneficial agent must be present in the device to maintain the desired rate of release over the given period of application. The maximum amount for safety purposes is determined by the requirement that the quantity of beneficial agent present cannot exceed a rate of release that reaches toxic levels.

Beneficial agent can be present in device 10 neat, or with other composition and lamina forming ingredients, such as a binder, dispersant, wetting agent, lubricant or dye. Representative of these include binders such as hydroxypropylmethyl cellulose, wetting agents such as fatty amines and fatty quaternary ammonium salts, and lubricants such as magnesium stearate and stearic acid.

Devices of this invention are designed for oral use, that is, for releasing a beneficial agent in the oral cavity of an animal, such as a human, over an extended period of time. Because the devices are designed to be retained in the mouth for periods on the order of about 0.5 to 12 hours, the devices must have an exterior shape which is comfortably retained in the mouth. It has been found that an cicular or oval disc shaped device is preferred from a comfort standpoint. As shown in FIGS. 1 and 2, device 10 has a length l, a width w, and a height h. It has been found that devices having a surface area defined by the length and width of 0.5 to 6 cm$^2$, preferably 0.5 to 2 cm$^2$, most preferably 1 cm$^2$, are most comfortably retained in the mouths of humans. In addition, in order to fit comfortably between the cheek and gum of a patient, the devices have a height of about 10 mils to 100 mils, preferably about 20 mils to about 40 mils, and most preferably about 25 mils.

The expressions "extended period of time" and "extended delivery period", as used herein, generally refer to periods greater than about 0.5 hours, preferably about 0.5 to 12 hours, more preferably about 1 to 6 hours, most preferably about 2–4 hours.

Generally, the device has from about 0.05 ng to 500 mg or more of beneficial agent, carrier, fillers, excipients, etc. with individual devices containing, for example, 0.25 mg, 1 mg, 5 mg, 125 mg, 250 mg, 500 mg, and the like. The device can be administered one to six times a day to a patient, preferably one to two times a day.

All patents and references given the specification are incorporated by reference.

The following examples are merely illustrative of the present invention and should not be considered as limiting the scope of the invention in any way.

EXAMPLE 1

A sustained release delivery devices for the controlled and continuous release into the oral cavity of the beneficial agent pilocarpine were made as follows: a composition comprising 10% pilocarpine, 72% ethylene vinyl acetate copolymer having a vinyl acetate content of 40% ("EVA 40") (USI and DuPont, USA), and 18% polyvinyl pyrrolidone ("PVP") (PVP K29-32, GAF Chemicals, USA) were added to an Internal Mixer with a 8 cc mixing bowl.

First, EVA 40 was added to the mixing bowl at 63° C. and mixed at 22 rpm until pellets were no longer visible. PVP was then slowly added to the mixing bowl. Addition time was approximately 11 minutes, during which the temperature was lowered to 52° C. Pilocarpine was then added to the mixing bowl. Addition time was approximately 3 minutes. The bowl was then closed and mixing continued for at least 20 minutes before removing the completed mix from the bowl.

Figure 6:
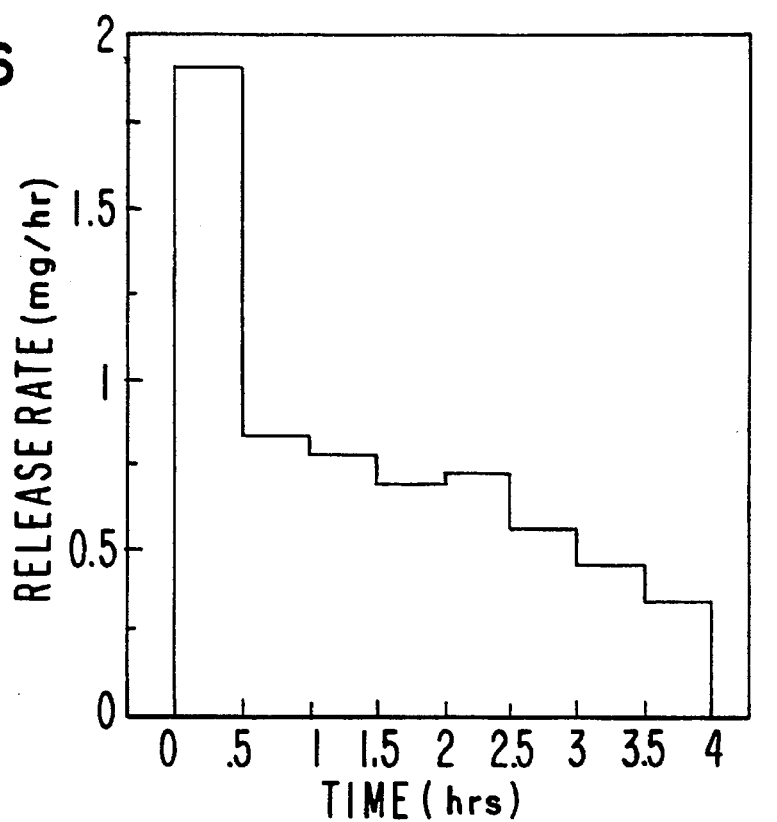
FIG. 6 is the rate of release of pilocarpine over four hours from an embodiment of this invention containing 72% ethylene vinyl acetate copolymer having a vinyl acetate content of 40%, 18% polyvinyl pyrrolidone and 10% pilocarpine.
Figure 7:
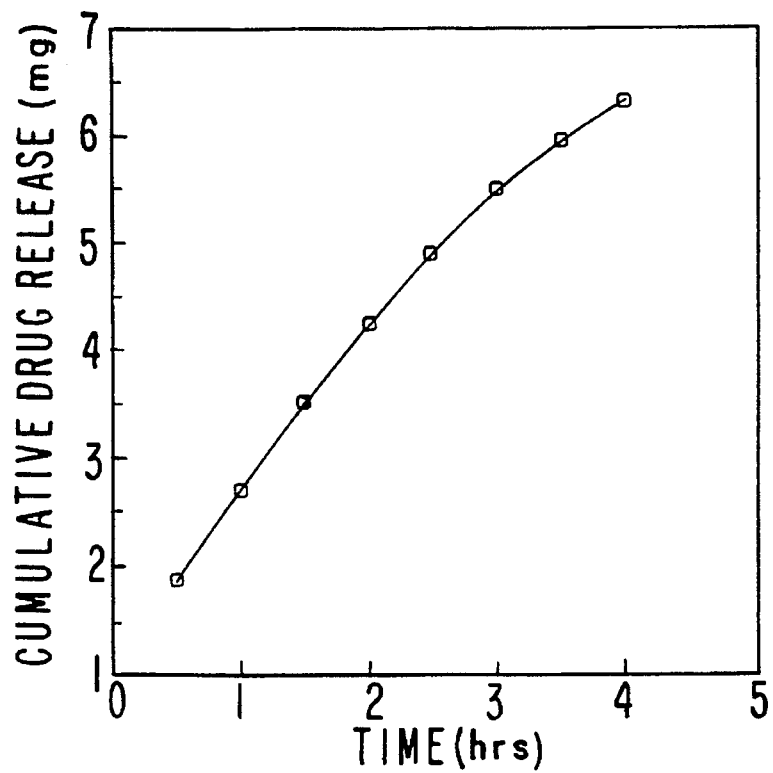
FIG. 7 is the cumulative amount of pilocarpine released over four hours from an embodiment of this invention containing 72% ethylene vinyl acetate copolymer having a vinyl acetate content of 40%, 18% polyvinyl pyrrolidone and 10% pilocarpine.

The mix was calendared to a 0.027" thickness film from which five 1 cm² discs were punched out of the film. The devices weighed an average of 67.4 mg. The release rates from the devices were determined. Each disc was attached to the flat side of the Teflon® holder of a release rate rod using nylon mesh and metal string. The rods were reciprocated in a fixed volume of receptor solution 0.05M so phosphate buffer, pH 6.5. The entire receptor solution was changed at each sampling time. The temperature of the receptor solution in the water bath was maintained at 37° C. The receptor solutions for each time interval were then assayed for pilocarpine, by HPLC, to calculate the release rate of pilocarpine from the device. The average rate of release of the devices over four hours is shown in FIG. 6. The average cumulative amount of pilocarpine released over four hours is shown in FIG. 7.

To treat xerostomia by local delivery of pilocarpine, the patient holds the sustained release device in his mouth for 3 to 4 hours. Two devices are used by the patient per 24 hours.

EXAMPLE 2

An osmotic therapeutic device, manufactured in the form of a delivery device for delivering pilocarpine into the oral cavity for an extended period of time, was manufactured as follows: first, an 8 g composition comprising 65% ethylene vinyl acetate copolymer having a vinyl acetate content of 28% ("EVA 28"), 25% PVP, and 10% pilocarpine were added to an Internal Mixer with a 8 cc mixing bowl.

First, EVA 28 was added to the mixing bowl at 63° C. and mixed at 22 rpm until pellets were no longer visible. PVP was then slowly added to the mixing bowl. Addition time was approximately 11 minutes during which the temperature was lowered to 52° C. Pilocarpine was then added to the mixing bowl. Addition time was approximately 3 minutes. The bowl was then closed and mixing continued for at least 20 minutes before removing the completed mix from the bowl.

Figure 8:
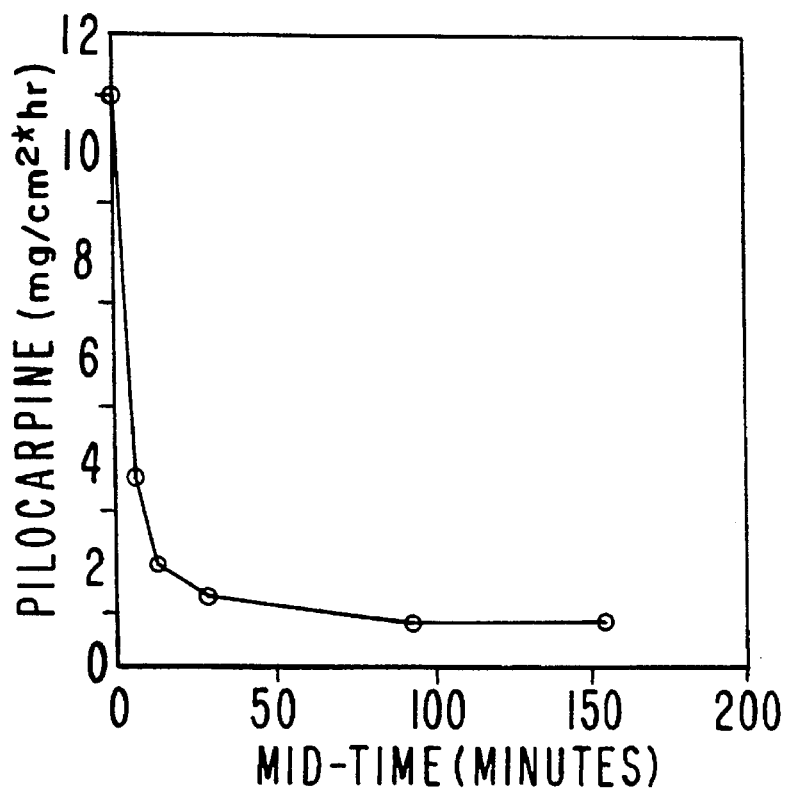
FIG. 8 is the rate of release of pilocarpine over four hours from an embodiment of this invention containing 65% ethylene vinyl acetate copolymer having a vinyl acetate content of 28%, 25% polyvinyl pyrrolidone and 10% pilocarpine.
Figure 9:
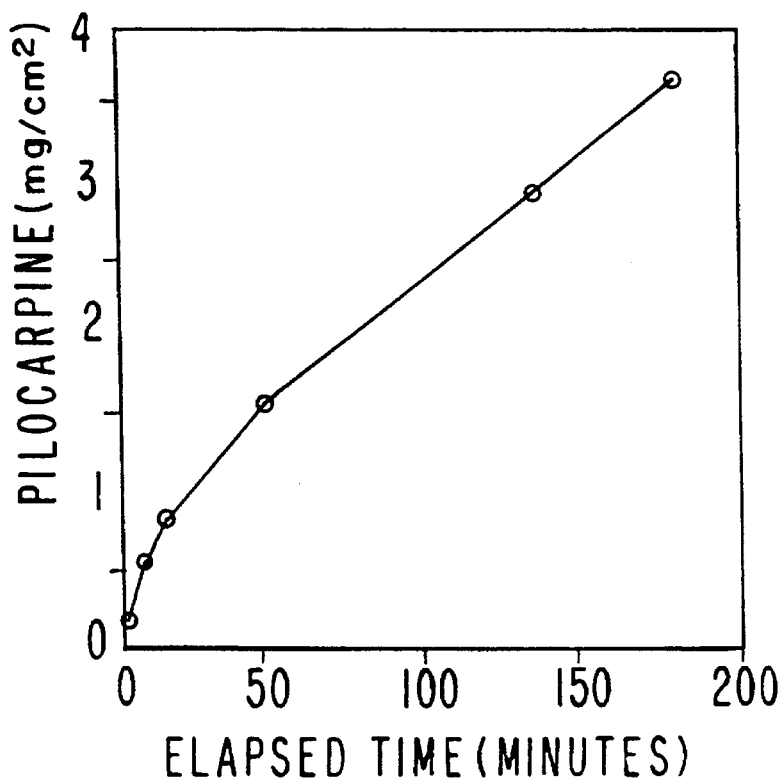
FIG. 9 is the cumulative amount of pilocarpine released over four hours from an embodiment of this invention containing 65% ethylene vinyl acetate copolymer having a vinyl acetate content of 28%, 25% polyvinyl pyrrolidone and 10% pilocarpine.

The mix was then hot pressed to a 0.027" thickness film. Three 1 cm² discs were punched out of the film. The release rate was then determined. Each disc was attached to the flat side of the Teflon® holder of a release rate rod using nylon mesh and metal string. The rods were reciprocated in a fixed volume of receptor solution 0.05M phosphate buffer, pH 6.5. The entire receptor solution was changed at each sampling time. The temperature of the receptor solution in the water bath was maintained at 37° C. The receptor solutions for each time interval were then assayed for pilocarpine, by HPLC, to calculate the release rate of pilocarpine from the device. The average rate of release of the devices over four hours is shown in FIG. 8. The average cumulative amount of pilocarpine released over four hours is shown in FIG. 9.

To treat xerostomia by local delivery of pilocarpine, the patient holds the sustained release device in his mouth for 3 to 4 hours. Two devices are used by the patient per 24 hours.

EXAMPLE 3

An osmotic therapeutic device, manufactured in the form of a delivery device for delivering pilocarpine into the oral cavity for an extended period of time, was manufactured as follows: first, an 8 g composition comprising 50% EVA 40, 40% PVP, and 10% pilocarpine were added to an Internal Mixer with a 8 cc mixing bowl.

First, EVA 28 was added to the mixing bowl at 60° C. and mixed at 22 rpm until pellets were no longer visible. PVP was then slowly added to the mixing bowl. Addition time was approximately 6 minutes. Mixing was continued for an additional 5 minutes. Pilocarpine was then added to the mixing bowl. Addition time was approximately 3 minutes. The bowl was then closed and mixing continued for 16 minutes before removing the completed mix from the bowl.

Figure 10:
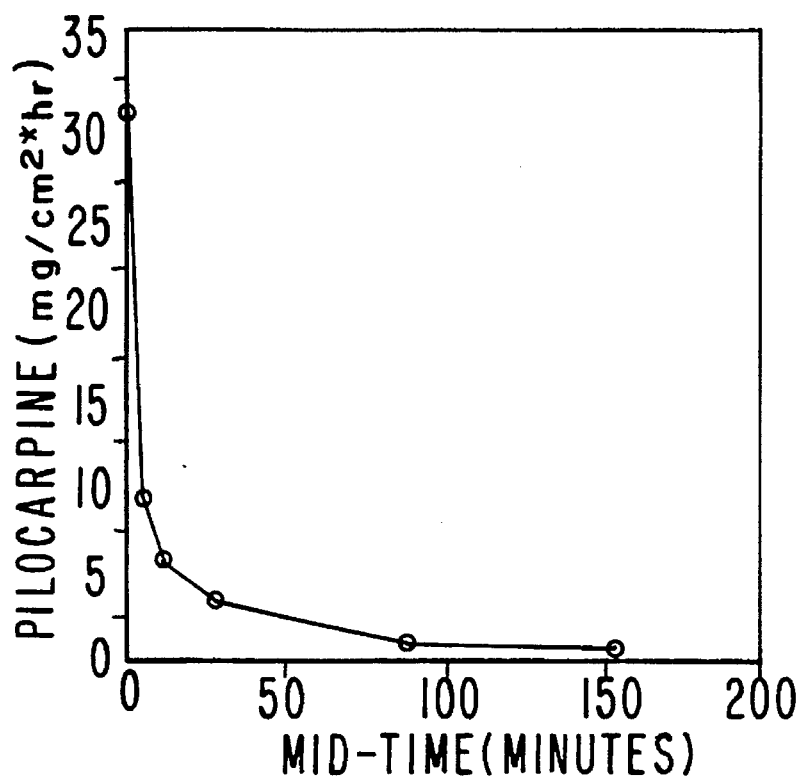
FIG. 10 is the rate of release of pilocarpine over four hours from an embodiment of this invention containing 50% ethylene vinyl acetate copolymer having a vinyl acetate content of 40%, 40% polyvinyl pyrrolidone and 10% pilocarpine.
Figure 11:
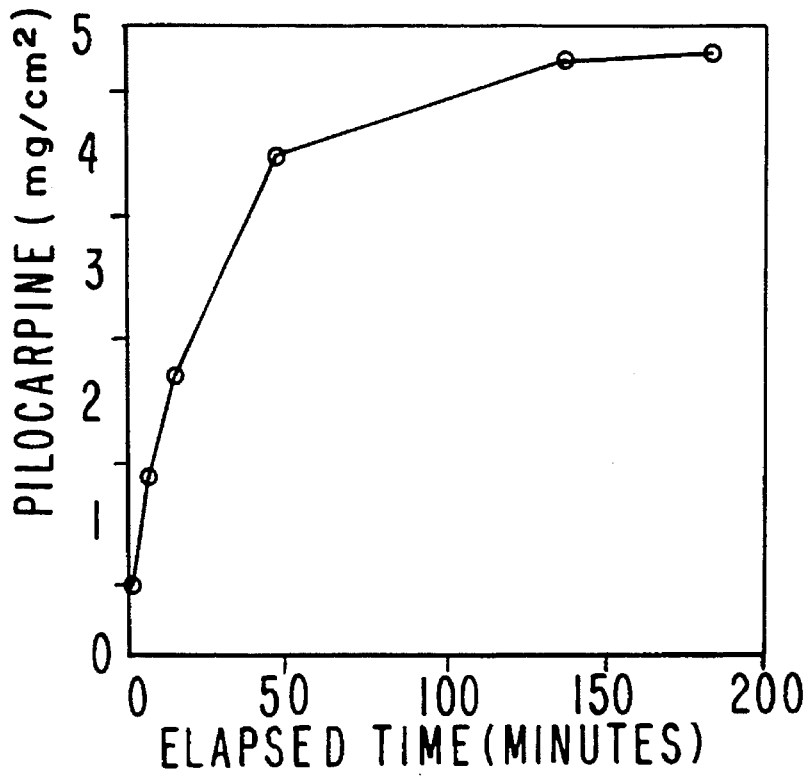
FIG. 11 is the cumulative amount of pilocarpine released over four hours from an embodiment of this invention containing 50% ethylene vinyl acetate copolymer having a vinyl acetate content as of 40%, 40% polyvinyl pyrrolidone and 10% pilocarpine.

The mix was calendared to a 0.025" thickness film. Three 1 cm² discs were punched out of the film. The release rate from the devices were determined. Each disc was attached to the flat side of the Teflon® holder of a release rate rod using nylon mesh and metal string. The rods were reciprocated in a fixed volume of receptor solution 0.05M phosphate buffer, pH 6.5. The entire receptor solution was changed at each sampling time. The temperature of the receptor solution in the water bath was maintained at 37° C. The receptor solutions for each time interval were then assayed for pilocarpine, by HPLC, to calculate the release rate of pilocarpine from the device. The average rate of release of the devices over four hours is shown in FIG. 10. The average cumulative amount of pilocarpine released over four hours is shown in FIG. 11.

To treat xerostomia by local delivery of pilocarpine, the patient holds the sustained release device in his mouth for 1 to 2 hours. Three devices are used by the patient per 24 hours.

EXAMPLE 4

An osmotic therapeutic device, manufactured in the form of a delivery device for delivering cetylpyridinium chloride into the oral cavity for an extended period of time, is manufactured as follows: first, an 8 g composition comprising 65% EVA 40, 25% PVP, and 10% cetylpyridinium chloride are added to an Internal Mixer with a 8 cc mixing bowl.

First, the EVA is added to the mixing bowl at 63° C. and mixed at 22 rpm until pellets were no longer visible. The PVP is then slowly added to the mixing bowl. Addition time is approximately 11 minutes during which the temperature is lowered to 52° C. Cetylpyridinium chloride is then added to the mixing bowl. Addition time is approximately 3 minutes. The bowl is then closed and mixing continued for at least 20 minutes before removing the completed mix from the bowl. The mix is pressed to a 0.027" thickness film and a device is cut from the film.

While there have been described and pointed out features of the invention as applied to the presently preferred embodiments, those skilled in the art will appreciate that various modifications, changes, additions and omissions in the systems illustrated and described can be made without departing from the spirit and scope of the invention, as defined in the appended claims.

What is claimed is:

1. A sustained release delivery device for administering beneficial agent continuously to the oral cavity of an animal for 0.5 to 12 hours at a controlled rate, said device comprising:

(a) a size and shape for comfortably retaining the device in the oral cavity for 0.5 to 12 hours; and (b) a matrix consisting essentially of about 0.1% to about 20% by weight beneficial agent, about 40% to about 95% by weight ethylene vinyl acetate copolymer having a vinyl acetate content of about 4% to about 80% and about 1% to about 60% by weight polyvinyl pyrrolidone.

2. A device according to claim 1 wherein the matrix contains about 45% to about 80% by weight ethylene vinyl acetate copolymer having a vinyl acetate content of about 20% to about 50% and about 10% to about 50% by weight polyvinyl pyrrolidone.

3. A device according to claim 1 wherein the matrix contains about 65% to about 80% by weight of ethylene vinyl acetate copolymer having a vinyl acetate content of about 25% to about 55%, about 15% to about 25% by weight polyvinyl pyrrolidone and about 1% to about 20% pilocarpine.

4. A device according to claim 1 where the extended period of time is from about 30 minutes to about 24 hours.

5. A device according to claim 1 where the extended period of time is from about 1 hour to about 6 hours.

6. A sustained release delivery device for administering beneficial agent continuously to the oral cavity of an animal for 0.5 to 12 hours at a controlled rate, said device comprising:
 (a) a size and shape for comfortably retaining the device in the oral cavity for 0.5 to 12 hours;
 (b) a matrix consisting essentially of about 0.1% to about 20% by weight beneficial agent, about 40% to about 95% by weight ethylene vinyl acetate copolymer having a vinyl acetate content of about 4% to about 80% and about 1% to about 60% by weight polyvinyl pyrrolidone; and
 (c) adhesive means for maintaining the matrix adhered to the mucosa of the oral cavity.

7. A device according to claim 6 wherein the matrix contains about 45% to about 80% by weight ethylene vinyl acetate copolymer having a vinyl acetate content of about 20% to about 50% and about 10% to about 50% by weight polyvinyl pyrrolidone.

8. A device according to claim 6 where the extended period of time is from about 30 minutes to about 24 hours.

9. A device according to claim 6 where the extended period of time is from about 1 hour to about 6 hours.

10. A device according to claim 6 wherein the means for maintaining the matrix adhered to the mucosa of the oral cavity comprises an in-line adhesive layer on the mucosal-proximal surface of the matrix.

11. A device according to claim 6 wherein the means for maintaining the matrix adhered to the mucosa is permeable to water.

12. A sustained release delivery device for administering beneficial agent continuously to the oral cavity of an animal for 0.5 to 12 hours at a controlled rate, said device comprising:
 (a) a size and shape for comfortably retaining the device in the oral cavity for 0.5 to 12 hours;
 (b) a matrix consisting essentially of about 0.1% to about 20% by weight beneficial agent, about 40% to about 95% by weight ethylene vinyl acetate copolymer having a vinyl acetate content of about 4% to about 80% and about 1% to about 60% by weight polyvinyl pyrrolidone;
 (c) a barrier that is impermeable to beneficial agent on the mucosa-distal surface of the matrix; and
 (d) adhesive means for maintaining the matrix adhered to the mucosa of the oral cavity.

13. A device according to claim 12 wherein the matrix contains about 45% to about 80% by weight ethylene vinyl acetate copolymer having a vinyl acetate content of about 20% to about 50% and about 10% to about 50% by weight polyvinyl pyrrolidone.

14. A device according to claim 12 where the extended period of time is from about 30 minutes to about 24 hours.

15. A device according to claim 12 where the extended period of time is from about 1 hour to about 6 hours.

16. A device according to claim 12 wherein the means for maintaining the matrix adhered to the mucosa of the oral cavity comprises an in-line adhesive layer on the mucosal-proximal surface of the matrix.

17. A device according to claim 12 wherein the adhesive means for maintaining the matrix adhered to the mucosa of the oral cavity is also the barrier that is impermeable to the beneficial agent and comprises an adhesive overlay on the mucosal-distal surface of the matrix.

18. A device according to claim 16 or 17 wherein the means for maintaining the matrix adhered to the mucosa is permeable to water.

19. A sustained release delivery device for administering beneficial agent continuously to the oral cavity of an animal for 0.5 to 12 hours at a controlled rate, said device comprising:
 (a) a size and shape for comfortably retaining the device in the oral cavity for 0.5 to 12 hours;
 (b) a matrix consisting essentially of about 0.1% to about 20% by weight beneficial agent, about 40% to about 95% by weight ethylene vinyl acetate copolymer having a vinyl acetate content of about 4% to about 80% and about 1% to about 60% by weight polyvinyl pyrrolidone;
 (c) a barrier that is impermeable to beneficial agent on the mucosa-proximal surface of the matrix; and
 (c) means for maintaining the matrix adhered to the mucosa of the oral cavity.

20. A device according to claim 19 wherein the matrix contains about 45% to about 80% by weight ethylene vinyl acetate copolymer having a vinyl acetate content of about 20% to about 50% and about 10% to about 50% by weight polyvinyl pyrrolidone.

21. A device according to claim 19 where the extended period of time is from about 30 minutes to about 24 hours.

22. A device according to claim 19 where the extended period of time is from about 1 hour to about 6 hours.

23. A device according to claim 19 wherein the means for maintaining the matrix adhered to the mucosa of the oral cavity comprises an in-line adhesive layer on the mucosal-proximal surface of the matrix.

24. A device according to claim 19 wherein the means for maintaining the matrix adhered to the mucosa of the oral cavity comprises an adhesive overlay on the mucosal-distal surface of the matrix.

25. A device according to claim 23 or 24 wherein the means for maintaining the matrix adhered to the mucosa is permeable to water.

\* \* \* \* \*